(12) United States Patent
Emerton et al.

(10) Patent No.: US 9,012,530 B2
(45) Date of Patent: Apr. 21, 2015

(54) BIOADHESIVE FOR PERIODONTAL GINGIVAL AND/OR BONE TISSUES

(75) Inventors: Kelly Brook Emerton, Memphis, TN (US); Susan J. Drapeau, Cordova, TN (US); Daniel Andrew Shimko, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 552 days.

(21) Appl. No.: 12/847,403

(22) Filed: Jul. 30, 2010

(65) Prior Publication Data

US 2012/0028219 A1 Feb. 2, 2012

(51) Int. Cl.
- A61F 13/00 (2006.01)
- A61K 9/00 (2006.01)
- A61C 19/06 (2006.01)
- A61Q 11/00 (2006.01)

(52) U.S. Cl.
CPC .......... *A61C 19/063* (2013.01); *A61K 9/00* (2013.01); *A61K 9/0063* (2013.01); *A61Q 11/00* (2013.01)

(58) Field of Classification Search
USPC .......... 523/111; 424/484; 433/39, 228.1; 606/214; 602/52
See application file for complete search history.

(56) References Cited

U.S. PATENT DOCUMENTS

| | | | |
|---|---|---|---|
| 3,277,891 A | 10/1966 | Hoey | |
| 3,696,811 A | 10/1972 | Chen | |
| 4,425,471 A | 1/1984 | Millet | |
| 4,752,472 A | 6/1988 | Kligman | |
| 4,836,879 A | 6/1989 | Edwards | |
| 5,006,410 A | 4/1991 | Vogel Viola et al. | |
| 5,093,179 A * | 3/1992 | Scantlebury et al. | 428/158 |
| 5,312,864 A | 5/1994 | Wenz et al. | |
| 5,393,368 A | 2/1995 | Stevens | |
| 5,792,508 A | 8/1998 | Kitamura et al. | |
| 6,146,655 A | 11/2000 | Ruben | |
| 6,201,088 B1 | 3/2001 | Gruber et al. | |
| 6,500,290 B1 | 12/2002 | Kao et al. | |
| 6,559,350 B1 * | 5/2003 | Tetreault et al. | 602/42 |
| 6,818,801 B2 | 11/2004 | Ashman | |
| 7,238,678 B2 | 7/2007 | Elson et al. | |
| 2001/0014831 A1 * | 8/2001 | Scarborough | 623/23.51 |
| 2004/0152039 A1 * | 8/2004 | Clegg et al. | 433/39 |
| 2005/0271694 A1 * | 12/2005 | Mansouri et al. | 424/423 |
| 2008/0051687 A1 * | 2/2008 | Rogers | 602/54 |
| 2011/0189253 A1 * | 8/2011 | Haddock et al. | 424/423 |

FOREIGN PATENT DOCUMENTS

WO WO 2009105637 A1 * 8/2009 ............. A61C 19/00

OTHER PUBLICATIONS

Dentsply/Caulk, Dentsply International Inc., Directions for Barricaid® vLC Periodontal Surgical Dressing, 1987 Milford, DE, 2 pages.

(Continued)

*Primary Examiner* — Michael Pepitone
(74) *Attorney, Agent, or Firm* — Sorell Lenna & Schmidt LLP

(57) ABSTRACT

The invention is directed to an adhesive strip, particularly an adhesive strip or bandage for use in periodontal treatments. The biocompatible adhesive strip comprises a flexible barrier with a biocompatible adhesive for use in an oral environment, wherein the adhesive is in a non-tacky state when dry and becomes adherent upon contact with liquids.

18 Claims, 4 Drawing Sheets

(56) References Cited

OTHER PUBLICATIONS

Abi Rached, et al., Reaction of the Human Gingival Tissue to Different Suture Materials used in Periodontal Surgery, Braz Dent J (1991) 2: 103-113.

Lim, Gas Permeable Membranes Composed of Carboxylated Poly(vinyl chloride) and Polyurethane, Bull. Korean Chem. Soc. 1999, vol. 20, No. 6, pp. 672-676, Faculty of Chemical Engineering & Technology, The Research Institute of Industrial Technology, Chonbuk National University, Chonju 561-756, Korea, Faculty of Biotechnology, Chonbuk National University, Chonju 561-756, Korea.

Dentsply DeTrey GmbH, Directions for Use Peripac® Periodontal Dressing, Konstantz, Germany, May 5, 1999, 2 pages.

\* cited by examiner

BIOADHESIVE FOR PERIODONTAL GINGIVAL AND/OR BONE TISSUES

BACKGROUND

Field of the Invention

The invention relates to a composition and method of treatment for wounds or tears in soft tissue, particularly periodontal gingival tissue.

It is desirable to seal and/or hold together wounded human or animal tissues, such as oral tissue. For example, a recent surgical site or wound is susceptible to infection and tissue healing is increased if the two sides of the surgical site are held in close proximity. Further, the act of chewing, saliva, and food and debris entering a surgical site or wound can delay clotting and healing. Lastly, due to the delicate nature and geometry of the gingival tissue post-tissue reflection, it is common to incur tears that are difficult to suture back together accurately. Therefore, an adhesive tape would greatly aid clinicians in sealing back together difficult wound sites.

Following oral surgery the incision is typically sutured and a cotton or gauze dressing may be placed on the surgical site. Such a dressing is frequently used to apply pressure to the wound to help stop bleeding and provide some protection against contaminants. However, a dressing that is made from an absorbent material has a limited ability to prevent moisture and saliva from reaching the surgical site and will become saturated with saliva. In addition, such dressings are typically held in place by either biting down or by wedging it between adjacent teeth, neither of which reliably hold the dressing in place. This results in the dressing being effective for only a few hours after surgery.

It would be desirable to have a dressing that prevents moisture from reaching a surgical site or wound, adequately seals the site from the environment, and be sufficiently adhesive to hold two sides of a wound in close proximity for a time that is sufficient to allow healing to begin.

There are a number of materials known that are moisture-wicking, biocompatible, and do not cause physical or chemical damage to the tissues. Biocompatible adhesives are also known and include powders, gums, polymers (e.g., cyanoacrylates) and other materials.

U.S. Pat. No. 1,550,425 describes a covering for protecting dental fillings in teeth. The covering consists of a thin metal foil with a layer of paraffin that is united to the foil by heat. On the outer surface of the paraffin there is a coating of finely ground gum tragacanth. Jelenko Company, Armonk, N.Y. sells a covering as Dryfoil™. The Jelenko product is reported to be 99.8% tin foil with a thickness of about 0.00075 inches or about 0.0013 inches.

However, the Burlew covering has been reported to have insufficient adhesiveness, preventing it from adhering to gingival tissue (see U.S. Pat. No. 6,818,801).

Thus, it would be desirable for such a covering to have increased capability to seal and protected tissues from the oral environment, which requires that the adhesive function well in an oral setting. Such and bandage or adhesive strip would also reduce or eliminate the need for suturing a wound in some instances.

Any publications or references discussed herein are presented to describe the background of the invention and to provide additional detail regarding its practice. Nothing herein is to be construed as an admission that the inventors are not entitled to antedate such disclosure by virtue of prior invention.

SUMMARY OF THE INVENTION

The present invention is directed to providing an adhesive strip, particularly an adhesive strip or bandage for use in periodontal treatments. The invention provides a biocompatible adhesive strip for use with human or animal tissues, and methods of producing the same.

The invention comprises a flexible barrier with a biocompatible adhesive for use in an oral environment. The adhesive is thus suitable for use with soft and/or hard tissues, such as gingival tissues in the mouth. The flexible barrier and adhesive form a strip that is easily applied to the tissues and preferably occupies minimal space. In an exemplary embodiment the barrier material and/or the adhesive are either substantially transparent or colored so as to blend in with the gum tissue it is adhered to. The adhesive strip may be contained in a dispenser as a continuous strip that can be pulled out of the container to a desired length and cut prior to or in conjunction with its application to the tissue. For example, the adhesive strip may be contained in a dispenser as a roll with a leading end projecting from the container. The dispenser may contain a mechanism for cutting the adhesive strip at a desired length, such as a cutting blade member, and/or the backing may have perforations extending from one side of the strip across to the other side such that the strip will easily tear along the perforations.

In an exemplary embodiment, the adhesive is in a non-tacky state when dry and becomes adherent upon contact with liquids, such as water or saliva. Thus, the barrier and adhesive may protect the tissue to promote healing and to minimize the possibility of blood clot breakdown, infection, or contamination when placed in a subject's mouth. In addition, the adhesive strip may be used in place of, or in combination with, sutures.

In an exemplary embodiment, the adhesive is located on one-sided of the barrier, wherein the adhesive is a cyanoacrylate adhesive that does not alter the healing process, has the ability to be removed and/or breaks down naturally. In an exemplary embodiment the adhesive non-radiation curable and composed of a single type of adhesive. Exemplary cyanoacrylate adhesives include, but are not limited to, n-butyl cyanoacrylate, isobutyl cyanoacrylate, and octyl cyanoacrylate. Cyanoacrylate adhesive also provide another benefit in that they are bacteriostatic. In another exemplary embodiment, the adhesive may comprise calcium sulfate, zinc sulfate, zink oxide, polymethyl methacrylate, dimethoxy tetraethylenglycol, and ascorbic acid.

In an exemplary embodiment, the barrier is made of a non-radiation transmitting material and does not expand or contract significantly in response to heat, moisture or light. Exemplary bio-resorbable barrier options, include, but are not limited to, gelatin, collagen, polysaccharides, xenograft, allograft, poly(ethylene glycol)-block-poly(epsilon-caprolactone)-block-poly(DL-lactide), PEG-PCL-P(DL) lactic acid, RGD-containing peptides (Arg-Gly-Asp) on a polyvinyl alcohol (PVA) surface, glycol-polymer matrix, heparin, alginate cross linked gels, agarose hydro-gels, a polyorthoester, polyaspirin, polyphosphazene, polyanhydride; polyketal, starch, pre-gelatinized starch, hyaluronic acid, chitosan, gelatin, alginate, albumin, fibrin, vitamin E analog, d-alpha tocopheryl succinate, poly-ϵ-caprolactone, dextran, polyvinylpyrrolidone, polyvinyl alcohol, PEGT-PBT copolymer, PEO-PPO-PEO, and sucrose acetate isobutyrate, carboxylated polyurethane membranes, expanded polytetrafluoroethylene (ePTFE) membranes, and/or combination thereof.

In another exemplary embodiment, the biocompatible adhesive comprises at least one therapeutic agent, for example, a growth factor and/or antibiotic (such as chlorohexidine and/or other such antibiotics) mixed in with the adhesive. The therapeutic agent being one that promotes healing of the underlying tissue and/or keeps the area around the adhesive strip relatively free of unwanted bacteria infection.

The barrier may be made so as to have aesthetic quality in the event it is placed in a visible area (e.g., the mouth), therefore transparent (substantially clear), or gum-tissue colored material may be utilized. The barrier may also be permeable to oxygen and relatively impermeable to water and/or saliva.

In another exemplary embodiment, the invention provides a periodontal treatment kit having at least one flexible adhesive strip and a surgical jelly that can be applied to the physicians glove and that is compatible with the barrier material of the adhesive strip so as to allow the physician to smooth the adhesive onto the tissue.

DETAILED DESCRIPTION OF THE INVENTION

Figure 1:
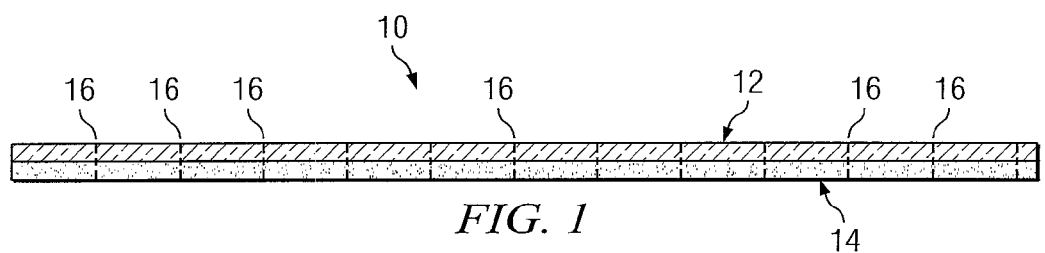
FIG. 1 is a side view of an exemplary adhesive strip.

For the purposes of promoting an understanding of the principles of the invention, reference will now be made to certain embodiments and specific language will be used to describe the same. It will nevertheless be understood that no limitation of the scope of the invention is thereby intended, such alterations and further modifications in the illustrated device, and such further applications of the principles of the invention as described herein being contemplated as would normally occur to one skilled in the art to which the invention relates.

The uses of the terms "a" and "an" and "the" and similar references in the context of describing the invention (especially in the context of the following claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

All methods described herein may be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, "comprising," "including," "containing," "characterized by," and grammatical equivalents thereof are inclusive or open-ended terms that do not exclude additional, unrecited elements or method steps, but will also be understood to include the more restrictive terms "consisting of" and "consisting essentially of."

As used herein, "biocompatible" means that the adhesive strip (the barrier material and adhesive) will not cause substantial tissue irritation or necrosis.

The adhesive strip is particularly advantageous for use in periodontal treatments. The adhesive strip may be trimmed to a desired size and/or shape to match the area to be covered. It is also desirable to produce the adhesive strip in a width that does not substantially interfere with oral function, e.g., speaking and chewing. For example, the adhesive strip may be manufactured with indentations or may be trimmed on site to have contoured edges that fit between adjacent teeth. In the embodiment having the contoured edge that generally follows the contour of patients teeth, the other lateral edge has not been contoured or trimmed.

In order to place the adhesive strip on the desired site, the adhesive strip is positioned over the desired location with the adhesive facing toward the soft tissue. The adhesive strip is applied against the gum tissue to isolate a surgical site from the oral environment or to hold torn or cut gum tissue in close proximity.

The invention, as illustrated in FIG. 1, comprises a flexible barrier 12 with a biocompatible adhesive 14 for use in an oral environment. The adhesive 14 is thus suitable for use with soft and/or hard tissues, such as gingival tissues in the mouth. The flexible barrier 12 and adhesive 14 form a strip 10 that is easily applied to the tissues and preferably occupies minimal space. In an exemplary embodiment the barrier material 12 and/or the adhesive 14 are either substantially transparent or colored so as to blend in with the gum tissue it is adhered to. In another exemplary embodiment, the barrier material 12 and adhesive 14 may be perforated 16 to facilitate tearing the strip 10 at predetermined locations.

Figure 2A:
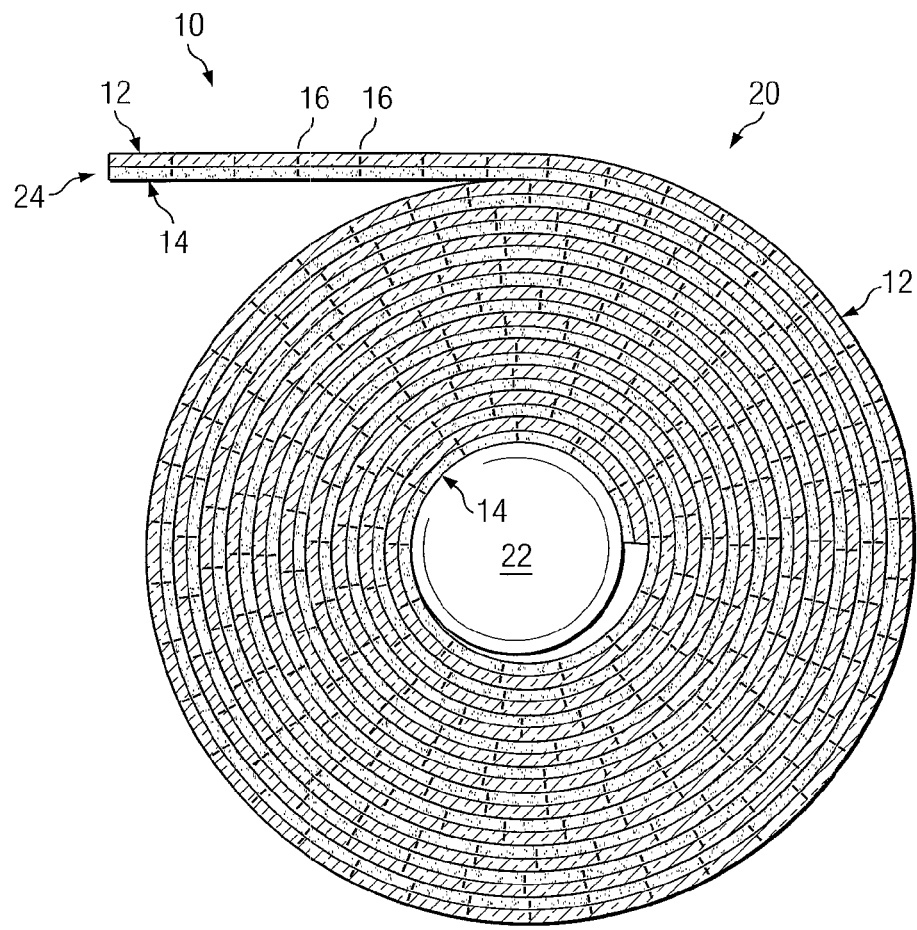
FIG. 2A is a side view of an exemplary adhesive strip packaged as a roll and FIG. 2B is a side view of an exemplary adhesive strip packaged as a roll with a carrying membrane interposed between one layer and the underlying layer of adhesive strip.
Figure 2B:
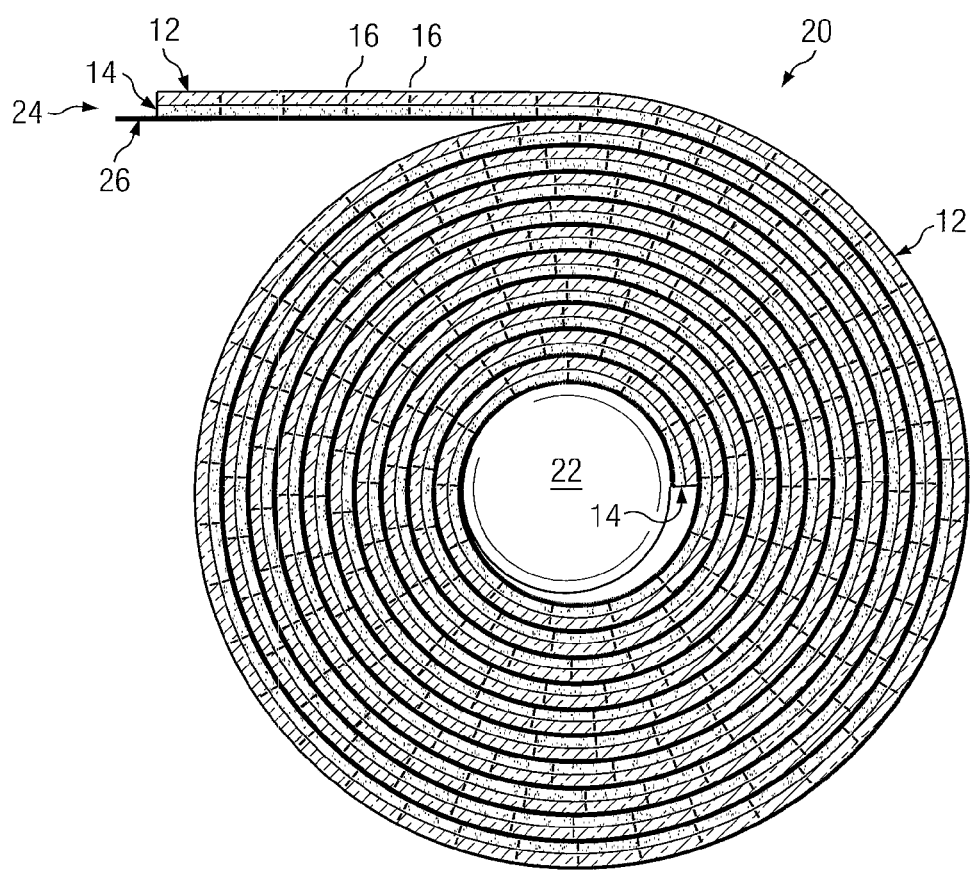

As illustrated in FIG. 2A and FIG. 2B, the adhesive strip 10 may be made into a roll 20 with a leading end 24 available to be unrolled and applied to tissue. In an exemplary embodiment, the adhesive 14 is maintained in a non-tacky state during storage, hence the roll 20 may be made by simply winding the strip 10 onto itself such that a top surface of the flexible barrier 12 is in contact with a bottom surface of the adhesive 14 above it (FIG. 2A). In another exemplary embodiment the strip 10 may have an additional carrying membrane 26 below the adhesive 14 such that the strip 10 comprises three layers, a top flexible barrier 12 in communication with an adhesive 14 resting on the carrying membrane 26. In this embodiment, the strip 10 may be formed into a roll 20 wherein the carrying membrane 26 resides between an underlying flexible barrier 12 layer and the adhesive layer 14 of the strip 10 portion overlaying it (FIG. 2B). In either embodiment, the strip 10 may be perforated 16 at predetermined sites to facilitate tearing of the strip 10 at that site, thereby allowing the user to select the appropriate length for use at any particular site. Perforations 16 may be beneficially used when the barrier 12 material is sufficiently strong so as to make tearing of the strip 10 difficult in the absence of such perforations 16.

In another exemplary embodiment, the strip 10 of FIGS. 1, 2A and 2B do not contain perforations 16. In this embodiment, the appropriate length may be obtained by cutting the strip 10 to a desired length, a container holding the strip may have a cutting member (not shown) configured to sever the strip 10, and/or the barrier material 12 (and adhesive 14) may be made of a material that is relatively easily torn.

In an exemplary embodiment, the flexible barrier 12 is made of a material selected from the group consisting of gelatin, collagen, poly(ethylene glycol)-block-poly(epsilon-caprolactone)-block-poly(DL-lactide), PEG-PCL-P(DL) lactic acid, RGD-containing peptides (Arg-Gly-Asp) on a polyvinyl alcohol (PVA) surface, glycol-polymer matrix, heparin, alginate cross linked gels, agarose hydro-gels, xenograft, allograft, polyorthoester, polyaspirin, polyphosphazene, polyanhydride; polyketal, collagen, starch, pre-gelatinized starch, hyaluronic acid, chitosan, gelatin, alginate, albumin, fibrin, vitamin E analog, d-alpha tocopheryl succinate, poly-ϵ-caprolactone, dextran, polyvinylpyrrolidone, polyvinyl alcohol, PEGT-PBT copolymer, PEO-PPO-PEO, sucrose acetate isobutyrate, expanded polytetrafluoroethylene (ePTFE) membranes, and/or combination thereof (e.g., see US Pat Pub 20090202604). In another exemplary embodiment the flexible barrier 12 comprises expanded polytetrafluoroethylene (ePTFE), wherein the pore size is sufficient to allow passage of oxygen to the underlying tissue, but small enough to prevent an aqueous phase, such as water or saliva, from reaching the underlying tissue. For example, medical grade Gore-Tex® provides such a barrier material 12. An additional benefit of such a material is that the pores allow integration of the underlying adhesive 14 into the barrier material 12 to facilitate joining of the adhesive layer 14 to the barrier material 12. The barrier may also be made of a polydimethylsiloxane (PDMS) membrane, carboxylated polyurethane (CPU) membrane, (see Lim et al. (1999) Gas Permeable Membranes Composed of Carboxylated Poly(vinyl chloride) and Polyurethane, *Bull. Korean Chem. Soc.* 20(6) 672-676).

In another exemplary embodiment, the strip 10 and/or roll 20 may be contained in a dispenser 30 (FIG. 3) as a strip 10 that can be pulled out of the dispenser 30 to a desired length in conjunction with its application to the tissue. For example, the adhesive strip 10 may be contained in a dispenser 34 as a roll 20 with a leading end 35 projecting from the dispenser 30. The dispenser may contain a mechanism for cutting the adhesive strip at a desired length (not shown), such as a cutting blade member, and/or the barrier 12 and adhesive 14 may have perforations extending from one side of the strip across to the other side such that the strip will easily tear along the perforations.

Figure 3:
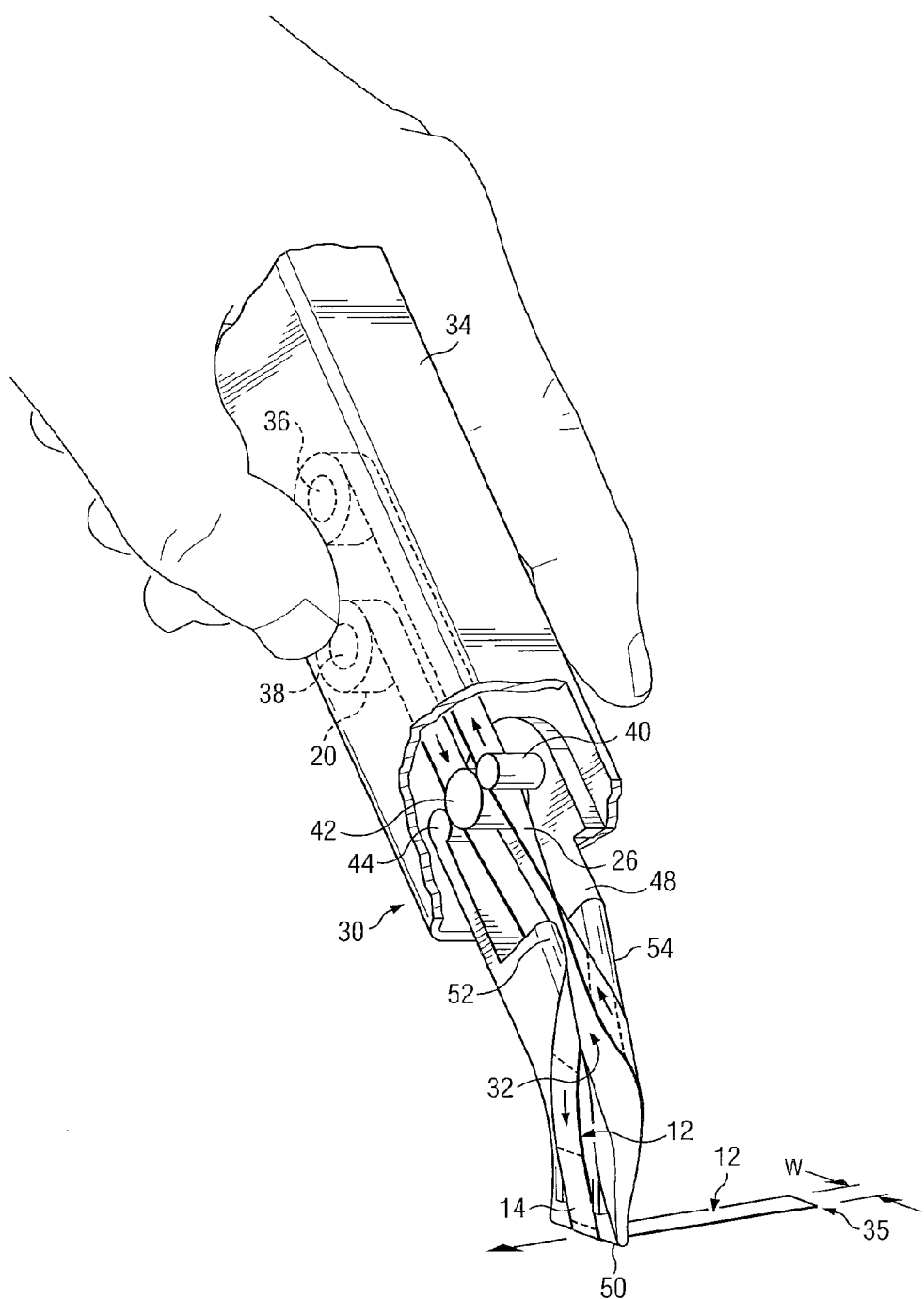
FIG. 3 is a perspective partial cross sectional view of an exemplary embodiment wherein the adhesive strip is contained in a dispenser.

The dispenser 30 illustrated in FIG. 3 has a housing 34 that contains the strip 10 supplied as a roll 20 on a dispensing spool 38 and a take-up spool 36. The spools 36, 38 are rotatable about their respective parallel axes and may be coupled by a slipping drive mechanism (not shown), where rotation of the dispensing spool 38 in response to the strip 10 being drawn out of the dispenser 30 causes the take-up spool 36 to rotate and take up the carrying membrane 26 at a rate equal to the rate at which the strip 10 is dispensed.

The housing may be of any configuration, so long as it has sufficient space to house the roll 20 and dispensing spool 38 along with the take-up spool 36. Protruding from the forward end of the housing is a dispensing tip 48 having a distal end defined by a leading edge 50, which allows the strip 10 to be pressed against tissue with the adhesive layer 14 in contact therewith. The strip 10 and/or carrying membrane 26 extend between the dispensing spool 38 and take-up spool 36 is configured to pass around the leading edge 50. A guiding mechanism to hold the strip 10 in the desired location may be provided by structures and methods known in the art, e.g., see U.S. Pat. No. 5,393,368.

As will be apparent from FIG. 3 the strip 10 comprises a barrier material 12, an adhesive 14 and a carrying membrane 26 configured such that when the strip 10 passed around the leading edge 50 the carrying member 26 is proximal to the leading edge 50, followed by the barrier material 12 and finally the adhesive layer 14, such that the adhesive layer 14 will come into contact with the moist surface of the tissue. Optionally, the carrying membrane 26 may be twisted 90° and pass between the guides 40 and 42, with the strip 10 (comprising the barrier 12, adhesive 14 and carrying membrane 26) may pass between guides 42 and 44. In light of the present description, it will now be understood that the carrying membrane 26 provides protection to the barrier membrane as it approaches the leading edge 50 of the dispensing tip 48. In addition, the adhesive layer is facing away from the surfaces of the leading edge 50, thereby reducing the chance that the adhesive will prematurely come in contact with a liquid environment and bind to the dispensing tip 48.

While FIG. 3 illustrates the dispensing tip 48 and leading edge 50 being relatively short, in an exemplary embodiment the housing 34 continues down over dispensing arms 52, 54 such that the leading edge 50 may be easily inserted into a subject's mouth and contacted with gum tissue therein without having to insert the full dispenser 30. Hence, the dispensing arms 52, 54 and leading edge 50 may be comprise an elongate assembly and may be curved.

In an exemplary embodiment, the adhesive 14 is in a non-tacky state when dry and becomes adherent upon contact with liquids, such as water or saliva. Thus, the barrier 12 and adhesive 14 may protect the tissue to promote healing and to minimize the possibility of blood clot breakdown, infection, or contamination when placed in a subject's mouth. In addition, the adhesive strip 10 may be used in place of, or in combination with, sutures (not shown).

In an exemplary embodiment, the adhesive 14 is located on one-sided of the barrier 12, wherein the adhesive 14 is a cyanoacrylate adhesive that does not alter the healing process, and has the ability to be removed and/or breaks down naturally. In an exemplary embodiment the adhesive 14 is non-radiation curable and composed of a single type of adhesive 14. Exemplary cyanoacrylate adhesives 14 include, but are not limited to, n-butyl cyanoacrylate, isobutyl cyanoacrylate, and octyl cyanoacrylate. Cyanoacrylate adhesive also provide another benefit in that they are bacteriostatic. In another exemplary embodiment, the adhesive 14 may comprise calcium sulfate, zinc sulfate, zink oxide, polymethyl methacrylate, dimethoxy tetraethylenglycol, and ascorbic acid.

In an exemplary embodiment, the barrier 12 is made of a non-radiation transmitting material and does not expand or contract significantly in response to heat or light. Exemplary bio-resorbable barrier materials 12, include, but are not limited to, gelatin, collagen, poly(ethylene glycol)-block-poly (epsilon-caprolactone)-block-poly(DL-lactide), PEG-PCL-P (DL) lactic acid, RGD-containing peptides (Arg-Gly-Asp) on a polyvinyl alcohol (PVA) surface, glycol-polymer matrix, heparin, alginate cross linked gels, agarose hydro-gels, xenograft, allograft, expanded polytetrafluoroethylene (ePTFE) membranes, and/or combination thereof.

The barrier 12 may be made so as to have aesthetic quality in the event it is placed in a visible area (e.g., the mouth), therefore transparent, or gum-tissue colored material may be utilized. The barrier 12 may also be permeable to oxygen and relatively impermeable to water and/or saliva. Likewise, the barrier 12 should be resistant to degradation in aqueous environments. Wherein the barrier 12 is resistant to degradation in an aqueous environment, the barrier 12 may be made from a biodegradable material that degrades or is absorbed over a period of time sufficient to allow the tissue to heal, for example, at least 3 days, at least 4 days, at least 5 days, at least 7 days, or at least two weeks.

Figure 4A:
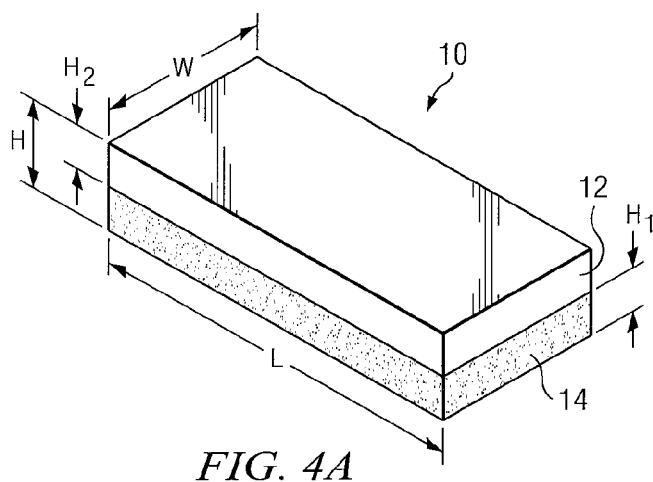
FIGS. 4A-C are perspective views of representative configurations of the adhesive strips of the invention.
Figure 4B:
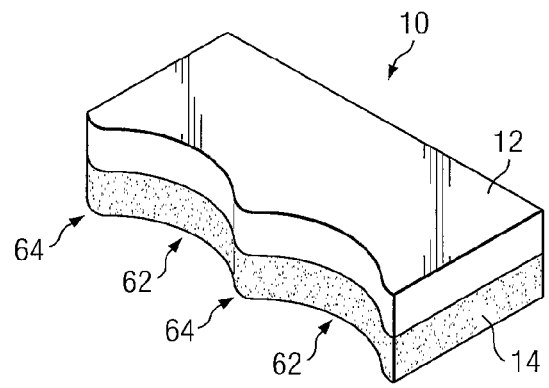
Figure 4C:
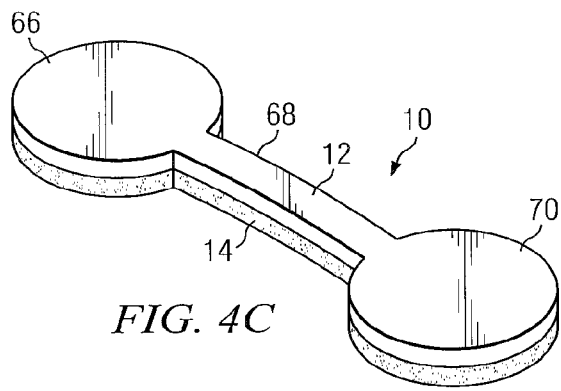

As illustrated in FIGS. 4A, B and C, the strip 10 may be fabricated or cut into many shapes. In an exemplary embodiment, the strip 10 is in a rectangular configuration as illustrated in FIG. 4A. In this configuration, the strip 10 has a length L, a width W and a height H (or thickness), wherein the height comprises the height $H_1$ of the adhesive 14, height $H_2$ of the barrier 12, and optionally the height (not shown) of the carrying membrane 26. In an exemplary embodiment, the height of the adhesive layer $H_1$ is less than 1 mm, less than 0.5 mm, less than 0.25 mm, or less than 0.01 mm. In an exemplary embodiment, the height of the barrier layer $H_2$ is less than 1 mm, less than 0.5 mm, less than 0.25 mm, or less than 0.01 mm. In another exemplary embodiment, the strip 10 (FIG. 47B) is made with recessed areas 62 and protruding areas 64 along an edge of the adhesive strip, wherein the recessed areas are configured to at least partially accept a patient's tooth and the protruding areas 64 are configured to reside at least partially between the teeth. In yet another exemplary embodiment, the strip 10 comprises a first end 66 having an enlarged surface area, a middle section 68 having a much smaller surface area to be able to go in between teeth and a second end having an enlarged surface area 70, configured such that the first and second ends 66, 70 can be connected to tissue in the mouth of a patient on either side of the tooth line and the middle section 68 can cover the area between two non-adjacent teeth, such as covering an area above a tooth extraction site thereby adhering papilla or other gum tissue together from buccal and lingual sides of the tooth line.

In yet another exemplary embodiment, the adhesive strip comprises a therapeutic agent that is capable of eluting from the adhesive strip, either the biocompatible adhesive, the barrier material or a combination thereof. The amounts of the elutable therapeutic agent for incorporation in the adhesive strip herein will depend on a number of factors well understood by those skilled in the art including the nature of the selected agents(s), the nature, amounts and configuration of the adhesive and/or barrier material and the desired profile (rate and duration) of release into the surrounding tissues. Again, empirical investigation employing known and conventional procedures can be utilized by those skilled in the art to arrive at an optimum concentration of specific agents(s) for a specific arrangement. The concentration of agents(s) and the elution profile will be such as to deliver a therapeutically effective concentration of the desired agents(s) for a therapeutically useful duration. Total concentration of deliverable agents can range, e.g., from about 0.1% to about 20%, and preferably about 1% to about 10%, weight percent of the carrier material (biocompatible adhesive, barrier and/or the combination thereof) and can provide eluted agent(s) in therapeutically useful amount for for at least 24 hours, at least 70, 100, 250, 500 or even 750 hours or more.

The therapeutic agent(s), incorporated in the adhesive strip herein include antibiotics which include, inter alia, anti-infective agents such as antiseptics, antiviral agents, and anti-fungal agents. Additional therapeutic agents include, but are not limited to, anti-inflammatory agents, local anesthetics and/or any of numerous other classes of therapeutic agents.

Any antibiotic suitable for use in a human may be used in accordance with various embodiments of the invention. The antibiotic may have bateriostatic and/or bacteriocidal activities. Non-limiting examples of classes of antibiotics that may be used include tetracyclines (e.g. minocycline), rifamycins (e.g. rifampin), macrolides (e.g. erythromycin), penicillins (e.g. nafcillin), cephalosporins (e.g. cefazolin), other beta-lactam antibiotics (e.g. imipenem, aztreonam), aminoglycosides (e.g. gentamicin), chloramphenicol, sufonamides (e.g. sulfamethoxazole), glycopeptides (e.g. vancomycin), quinolones (e.g. ciprofloxacin), fusidic acid, trimethoprim, metronidazole, clindamycin, mupirocin, polyenes (e.g. amphotericin B), azoles (e.g. fluconazole) and beta-lactam inhibitors (e.g. sulbactam). Non-limiting examples of specific antibiotics that may be used include minocycline, rifampin, erythromycin, nafcillin, cefazolin, imipenem, aztreonam, gentamicin, sulfamethoxazole, vancomycin, ciprofloxacin, chlorohexidine, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, and nystatin. Other examples of antibiotics, such as those listed in U.S. Pat. No. 4,642,104, the entire contents of which are incorporated by reference herein, may also be used. One of ordinary skill in the art will recognize other antibiotics that may be used.

Any anti-inflammatory agent suitable for use in a human may be used in accordance with various embodiments of the invention. Non-limiting examples of anti-inflammatory agents include steroids, such as cortisone, hydrocortisone, prednisone, dexamethasone, methyl-prednisilone, and derivatives thereof; and non-steroidal anti-inflammatory agents (NSAIDs). Non-limiting examples of NSAIDS include ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketorolac, flufenisal, salsalate, triethanolamine salicylate, aminopyrine, antipyrine, oxyphenbutazone, apazone, cintazone, flufenamic acid, clonixerl, clonixin, meclofenamic acid, flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate.

Any local anesthetic agent suitable for use in a human may be used in accordance with various embodiments of the invention. Non-limiting examples of local anesthetics agents include lidocaine, prilocaine, mepivicaine, benzocaine, bupivicaine, amethocaine, lignocaine (lidocaine), cocaine, cinchocaine, dibucaine, etidocaine, procaine, veratridine (selective c-fiber blocker) and articaine.

Any growth factor suitable for use in a human may be used in accordance with various embodiments of the invention. Non-limiting examples of growth factors include active forms of OP-1, OP-2, OP-3, BMP-2, BMP-3, BMP-4, BMP-5, BMP-6, BMP-9, BMP-10, BMP-11, BMP-13, BMP-15, GDF-1, GDF-3, GDF-5, GDF-6, GDF-7, bFGF, TGF-b, PDGF-BB, IGF-1, EGF, VEGF, and/or amino acid sequence variants thereof. See U.S. Patent Pubs. 2008/0014250 and 2009/0048412.

In addition, therapeutic agents may include, but are not limited to, xenograft, and/or allograft.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all publications cited herein are hereby incorporated by reference in their entirety.

What is claimed is:

1. A flexible adhesive strip comprising:
   a flexible barrier material having a first side and an opposite second side, the barrier material selected from the group consisting of gelatin, collagen, polysaccharides, poly(ethylene glycol)-block-poly(epsilon-caprolactone)-block-poly(DL-lactide), PEG-PCL-P(DL) lactic acid, RGD-containing peptides (Arg-Gly-Asp) on a polyvinyl alcohol (PVA) surface, glycol-polymer matrix, heparin, alginate cross linked gels, agarose hydro-gels, carboxylated polyurethane (CPU) membrane, expanded polytetrafluoroethylene (ePTFE) membranes, and combination thereof; and
   a biocompatible adhesive comprising a cyanoacrylate adhesive compatible with an aqueous oral environment, the biocompatible adhesive including a first side and an opposite second side, the first side of the biocompatible adhesive being adhered to the second side of the flexible barrier material,
   wherein the first side of the flexible barrier material is uncovered and the biocompatible adhesive is in a non-tacky state when dry and becomes adherent upon contact with a liquid, and
   wherein the flexible barrier material is substantially clear.

2. The flexible adhesive strip of claim 1, further comprising a first series of perforations formed in the flexible adhesive strip extending through opposite surfaces of flexible adhesive strip and a second series of perforations formed in the flexible adhesive strip extending through the opposite surfaces of the flexible adhesive strip that is spaced apart from the first series of perforations, the first and second series of perforations being configured to facilitate tearing of the flexible adhesive strip at the site of the perforations.

3. The flexible adhesive strip of claim 1, wherein the flexible adhesive strip comprises at least two recessed areas and protruding areas along a first edge, wherein the at least two recessed areas are configured to at least partially accept a patient's tooth and the protruding areas are configured to reside at least partially between the teeth.

4. The flexible adhesive strip of claim 1, wherein the flexible adhesive strip comprises a first end having an enlarged surface area, a middle section having a smaller surface area and a second end having an enlarged surface area, wherein the first and second ends are configured to be connected to tissue in the mouth of a patient on either side of a tooth line and the middle section is configured to cover an area between two non-adjacent teeth.

5. The flexible adhesive strip of claim 1, wherein the barrier material comprises an expanded polytetrafluoroethylene (ePTFE) membrane.

6. The flexible adhesive strip of claim 1, wherein the biocompatible adhesive further comprises a fibrin glue, a denture adhesive or a combination thereof.

7. The flexible adhesive strip of claim 1, wherein the cyanoacrylate adhesive comprises an octyl ester cyanoacrylate adhesive.

8. The flexible adhesive strip of claim 1, further comprising a therapeutic agent in combination with the biocompatible adhesive.

9. The flexible adhesive strip of claim 8, wherein the therapeutic agent comprises a growth factor or an antibiotic.

10. The flexible adhesive strip of claim 9, wherein the therapeutic agent comprises a growth factor selected from the group consisting of OP-1, BMP-2, GDF-5, PDGF, βFGF, TGF-β and combinations thereof.

11. The flexible adhesive strip of claim 9, wherein the therapeutic agent comprises chlorohexidine.

12. The flexible adhesive strip of claim 7, further comprising chlorohexidine.

13. The flexible adhesive strip of claim 8, wherein the therapeutic agent is an analgesic.

14. A periodontal treatment kit, comprising:
    at least one flexible adhesive strip of claim 1; and
    a surgical jelly compatible with the barrier material of the adhesive strip.

15. The periodontal treatment kit of claim 14, wherein the biocompatible adhesive comprises cyanoacrylate adhesive, a fibrin glue, a denture adhesive or combinations thereof.

16. The flexible adhesive strip of claim 1, wherein the flexible barrier material has a thickness of less than 1 mm and the biocompatible adhesive has a thickness of less than 1 mm.

17. The flexible adhesive strip of claim 1, wherein the biocompatible adhesive comprises calcium sulfate, zinc sulfate, zinc oxide, dimethoxy tetraethylenglycol, or ascorbic acid.

18. The flexible adhesive strip of claim 16, wherein the biocompatible adhesive comprises calcium sulfate, zinc sulfate, zinc oxide, dimethoxy tetraethylenglycol, or ascorbic acid.

* * * * *